United States Patent
DeLuca et al.

(10) Patent No.: US 7,704,982 B2
(45) Date of Patent: Apr. 27, 2010

(54) 2-METHYLENE-19-NOR-1α-HYDROXY-17-ENE-HOMOPREGNACALCIFEROL AND ITS USES

(75) Inventors: Hector F. DeLuca, Deerfield, WI (US); Bulli Padmaja Tadi, Madison, WI (US); Lori A. Plum, Arena, WI (US); Margaret Clagett-Dame, Deerfield, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 70 days.

(21) Appl. No.: 11/775,117

(22) Filed: Jul. 9, 2007

(65) Prior Publication Data

US 2007/0249569 A1    Oct. 25, 2007

Related U.S. Application Data

(63) Continuation of application No. 11/283,125, filed on Nov. 18, 2005, now Pat. No. 7,241,750.

(60) Provisional application No. 60/630,007, filed on Nov. 22, 2004.

(51) Int. Cl.
*A61K 31/59* (2006.01)
*C07C 401/00* (2006.01)

(52) U.S. Cl. ........................ 514/167; 552/653

(58) Field of Classification Search ................ 552/653; 514/167
See application file for complete search history.

(56) References Cited

U.S. PATENT DOCUMENTS

| | | |
|---|---|---|
| 5,141,927 A | 8/1992 | Krotkiewski |
| 5,145,846 A | 9/1992 | Baggiolini et al. |
| 5,292,727 A | 3/1994 | Godtfredsen |
| 5,362,719 A | 11/1994 | Godtfredsen |
| 5,545,633 A | 8/1996 | Bretting |

(Continued)

FOREIGN PATENT DOCUMENTS

WO    02/094247    11/2002

(Continued)

OTHER PUBLICATIONS

Kamycheva et al, "Intakes of Calcium and Vitamin D Predict Body Mass Index in the Population of Northern Norway," The Journal of Nutrition, 2002.

(Continued)

*Primary Examiner*—Sabiha Qazi
(74) *Attorney, Agent, or Firm*—Andrus, Sceales, Starke & Sawall, LLP

(57) ABSTRACT

This invention discloses 2-methylene-19-nor-17-ene vitamin D analogs, and specifically 2-methylene-19-nor-1α-hydroxy-17-ene-homopregnacalciferol and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders and inflammatory diseases in humans as well as renal osteodystrophy. This compound may also be used for the treatment or prevention of obesity.

30 Claims, 6 Drawing Sheets

$K_i$:  $1,25(OH)_2D_3 = 7.8 \times 10^{-11}$ M
VIT-I (2-methylene-19-nor-1α-hydroxy-17-ene-homopregnacalciferol) = $1.9 \times 10^{-10}$ M

U.S. PATENT DOCUMENTS

| | | | |
|---|---|---|---|
| 5,843,928 | A | 12/1998 | Deluca et al. |
| 5,929,056 | A | 7/1999 | Mourino et al. |
| 5,936,105 | A * | 8/1999 | Paaren .................. 552/653 |
| 5,945,410 | A | 8/1999 | DeLuca et al. |
| 6,028,208 | A | 2/2000 | Gao et al. |
| 6,316,642 | B1 | 11/2001 | DeLuca et al. |
| 6,399,797 | B1 | 6/2002 | von Daehne et al. |
| 6,579,861 | B2 | 6/2003 | DeLuca et al. |
| 6,627,622 | B2 | 9/2003 | DeLuca et al. |
| 6,844,330 | B2 * | 1/2005 | DeLuca et al. ............. 514/167 |
| 6,887,860 | B2 | 5/2005 | DeLuca et al. |
| 6,939,868 | B2 | 9/2005 | DeLuca et al. |
| 6,992,074 | B2 | 1/2006 | DeLuca et al. |
| 7,241,749 | B2 | 7/2007 | DeLuca et al. |
| 7,241,750 | B2 | 7/2007 | DeLuca et al. |
| 2005/0119242 | A1 | 6/2005 | DeLuca et al. |
| 2005/0143358 | A1 | 6/2005 | DeLuca et al. |
| 2007/0238702 | A1 | 10/2007 | DeLuca et al. |

FOREIGN PATENT DOCUMENTS

| | | |
|---|---|---|
| WO | 2004/080922 | 9/2004 |
| WO | 2005/018648 | 3/2005 |
| WO | WO 2005/051323 | 6/2005 |

OTHER PUBLICATIONS

Arunabh et al, "Body Fat Content and 25-Hydroxyvitamin D Levels in Healthy Women," The Journal of Clinical Endocrinology & Metabolism, 2003, 88(1): 157-161.

DeLuca, H.F. "*Therapeutic Potential of the 2-Alkyl and 2-Alkylidene-19-Nor-(20S)-Modified Analogs of 1α,25-Dihydroxyvitamin $D_3$,*" May 1, 2004, Journal of Steroid Biochemistry and Molecular Biology, Elsevier Science Ltd., Oxford, vol. 89/90, No. 1-5.

* cited by examiner

EC$_{50}$: 1,25(OH)$_2$D$_3$ = 6.2 x 10$^{-9}$ M

VIT-I (2-methylene-19-nor-1α-hydroxy-17-ene-homopregnacalciferol) = 1.3 x 10$^{-8}$ M

2-METHYLENE-19-NOR-1α-HYDROXY-17-ENE-HOMOPREGNACALCIFEROL AND ITS USES

CROSS REFERENCE TO RELATED APPLICATION

This application is a continuation of U.S. patent application Ser. No. 11/283,125, filed Nov. 18, 2005, now U.S. Pat. No. 7,241,750.

This application claims priority to U.S. Provisional Application No. 60/630,007, filed Nov. 22, 2004.

BACKGROUND OF THE INVENTION

This invention relates to vitamin D compounds, and more particularly to 2-methylene-19-nor-1α-hydroxy-17-ene-homopregnacalciferol and its pharmaceutical uses.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 2-methylene-19-nor-17-ene-vitamin D analogs, and more specifically toward 2-methylene-19-nor-1α-hydroxy-17-ene-homopregnacalciferol, their biological activity, and various pharmaceutical uses for these compounds.

Structurally these 2-methylene-19-nor-17-ene-vitamin D analogs are characterized by the general formula I shown below:

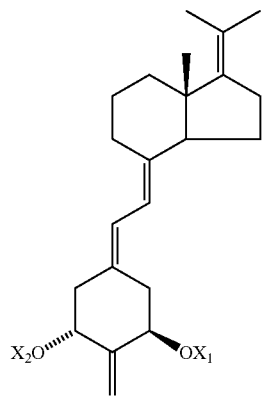

I where $X_1$ and $X_2$, which may be the same or different, are each selected from hydrogen or a hydroxy-protecting group. The preferred analog is 2-methylene-19-nor-1α-hydroxy-17-ene-homopregnacalciferol which has the following formula Ia:

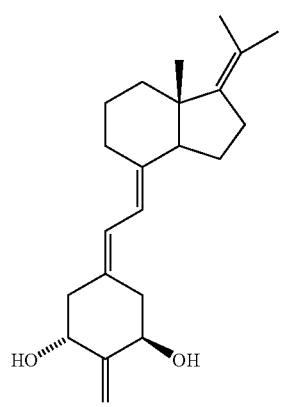

Ia

The above compounds I, and particularly Ia, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the pre-proparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism of renal osteodystrophy.

The compounds I, and particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of VIT-I and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of VIT-I and 1,25$(OH)_2D_3$;

FIG. 3 is a graph illustrating the in vitro transcription activity of 1,25$(OH)_2D_3$ as compared to VIT-I;

FIGS. 4 and 5 are bar graphs illustrating the bone calcium mobilization activity of 1,25$(OH)_2D_3$ as compared to VIT-I. Each graph represents a separate batch of vitamin D-deficient animals. The results depicted in FIG. 5 are not vehicle-controlled, but rather each animal serves as its own control because the animals were bled pre- and post-dose; and FIG. 6 is a bar graph illustrating the intestinal calcium transport activity of 1,25$(OH)_2D_3$ as compared to VIT-I.

Figure 1:
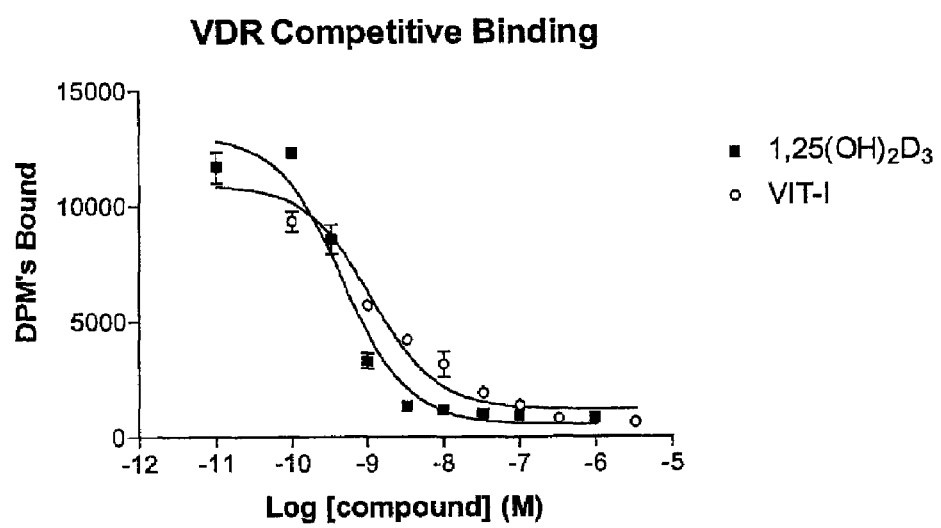
FIGS. 1-6 illustrate various biological activities of 2-methylene-19-nor-1α-hydroxy-17-ene-homopregnacalciferol, hereinafter referred to as "VIT-I," as compared to the native hormone 1α,25-dihydroxyvitamin $D_3$, hereinafter "1,25 $(OH)_2D_3$."

DETAILED DESCRIPTION OF THE INVENTION 2-methylene-19-nor-1α-hydroxy-17-ene-homopregnacalciferol (referred to herein as VIT-I) was synthesized and tested. Structurally, this 19-nor analog is characterized by the general formula Ia previously illustrated herein, and its prodrug (in protected hydroxy form) by the formula I.

The preparation of 2-methylene-19-nor-1α-hydroxy-17-ene-homopregnacalciferol having the structure Ia as well as analogs I can be accomplished by a common general method, i.e. the condensation of a bicyclic Windaus-Grundmann type ketone II with the allylic phosphine oxide III to the corresponding 2-methylene-19-nor-17-ene-vitamin D analog IV followed by deprotection at C-1 and C-3 to provide Ia:

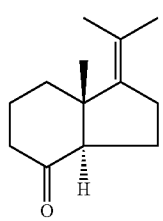

II

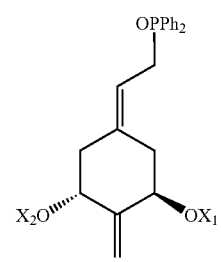

III

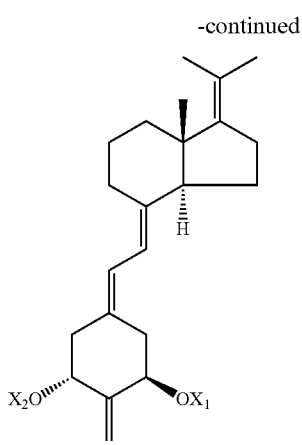

IV

In the structures III and IV, groups $X_1$ and $X_2$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown on the Scheme herein (see the preparation of compound VIT-1).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I, Ia, II, III and IV is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O-CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following description as well as to Scheme 1 herein for a detailed illustration of the preparation of compound VIT-I.

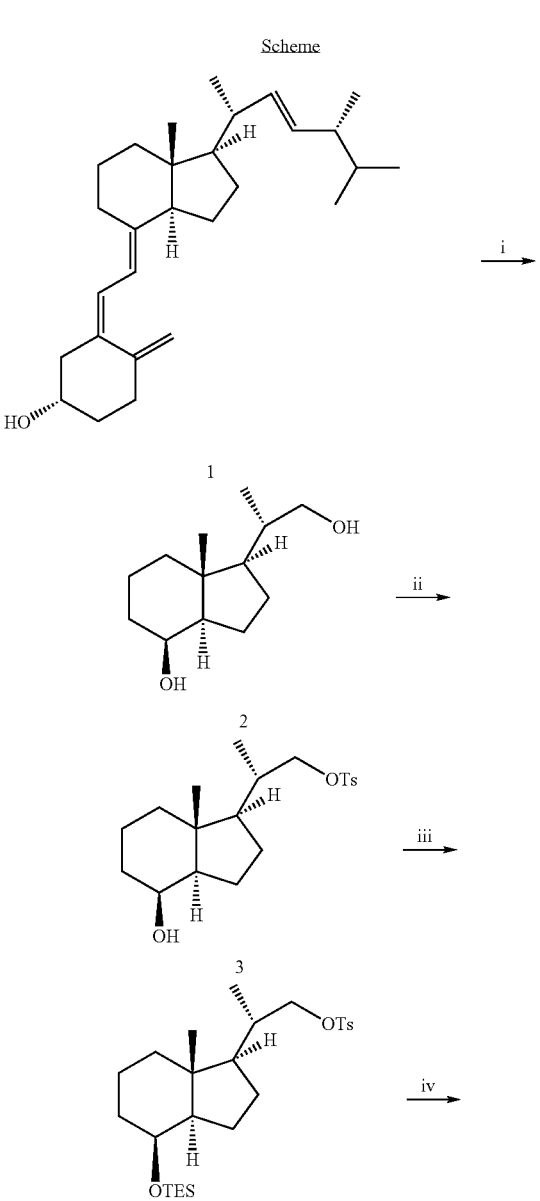

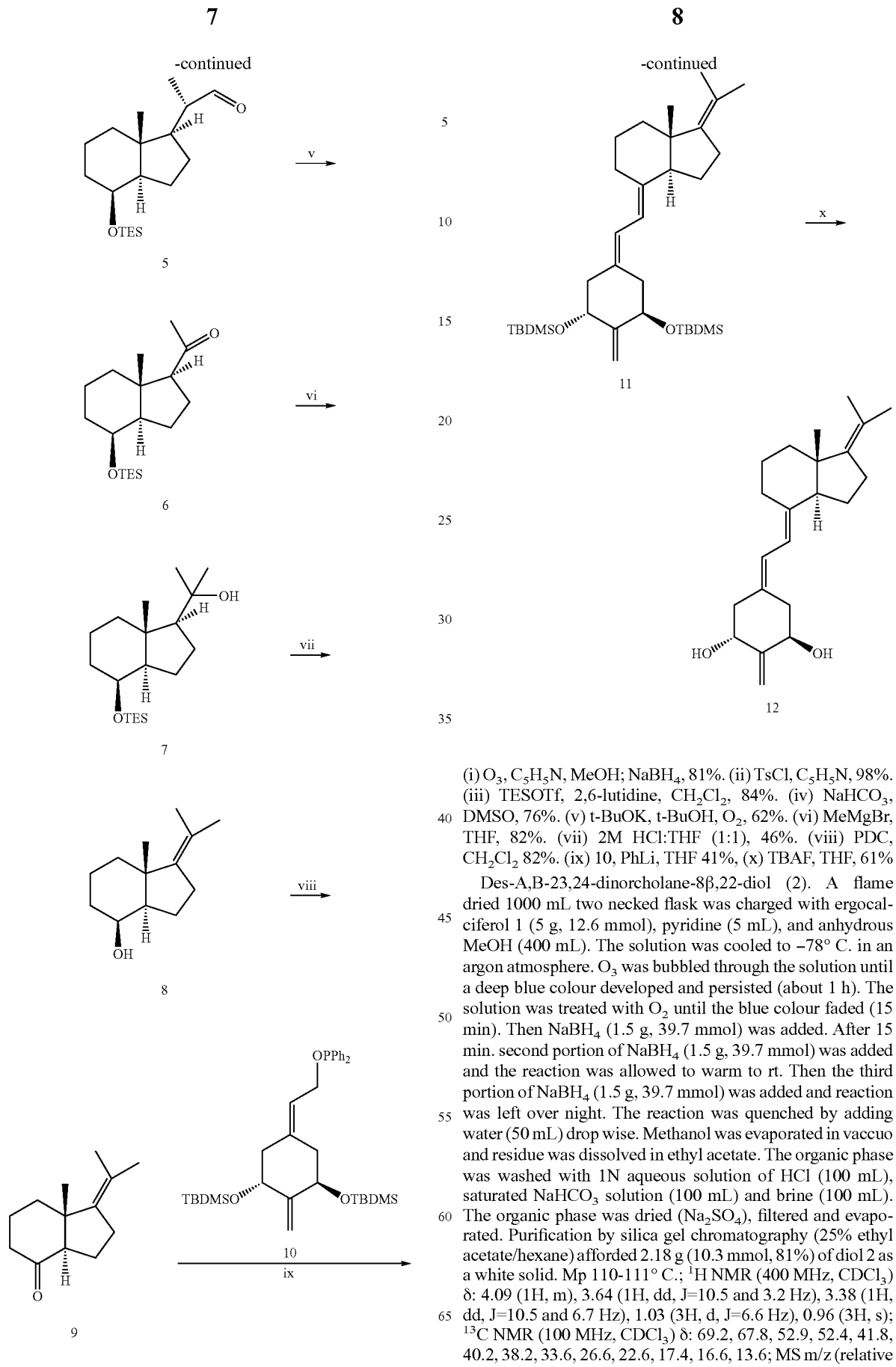

(i) $O_3$, $C_5H_5N$, MeOH; $NaBH_4$, 81%. (ii) TsCl, $C_5H_5N$, 98%. (iii) TESOTf, 2,6-lutidine, $CH_2Cl_2$, 84%. (iv) $NaHCO_3$, DMSO, 76%. (v) t-BuOK, t-BuOH, $O_2$, 62%. (vi) MeMgBr, THF, 82%. (vii) 2M HCl:THF (1:1), 46%. (viii) PDC, $CH_2Cl_2$ 82%. (ix) 10, PhLi, THF 41%, (x) TBAF, THF, 61%

Des-A,B-23,24-dinorcholane-8β,22-diol (2). A flame dried 1000 mL two necked flask was charged with ergocalciferol 1 (5 g, 12.6 mmol), pyridine (5 mL), and anhydrous MeOH (400 mL). The solution was cooled to −78° C. in an argon atmosphere. $O_3$ was bubbled through the solution until a deep blue colour developed and persisted (about 1 h). The solution was treated with $O_2$ until the blue colour faded (15 min). Then $NaBH_4$ (1.5 g, 39.7 mmol) was added. After 15 min. second portion of $NaBH_4$ (1.5 g, 39.7 mmol) was added and the reaction was allowed to warm to rt. Then the third portion of $NaBH_4$ (1.5 g, 39.7 mmol) was added and reaction was left over night. The reaction was quenched by adding water (50 mL) drop wise. Methanol was evaporated in vaccuo and residue was dissolved in ethyl acetate. The organic phase was washed with 1N aqueous solution of HCl (100 mL), saturated $NaHCO_3$ solution (100 mL) and brine (100 mL). The organic phase was dried ($Na_2SO_4$), filtered and evaporated. Purification by silica gel chromatography (25% ethyl acetate/hexane) afforded 2.18 g (10.3 mmol, 81%) of diol 2 as a white solid. Mp 110-111° C.; $^1$H NMR (400 MHz, $CDCl_3$) δ: 4.09 (1H, m), 3.64 (1H, dd, J=10.5 and 3.2 Hz), 3.38 (1H, dd, J=10.5 and 6.7 Hz), 1.03 (3H, d, J=6.6 Hz), 0.96 (3H, s); $^{13}$C NMR (100 MHz, $CDCl_3$) δ: 69.2, 67.8, 52.9, 52.4, 41.8, 40.2, 38.2, 33.6, 26.6, 22.6, 17.4, 16.6, 13.6; MS m/z (relative integration): 212 (M+, 2), 194 (15), 179 (18), 125 (43), 111 (100); exact mass calculated for $C_{13}H_{22}O$ ([M-H$_2$O]+) is 194.1671, found 194.1665.

Des-A,B-22-(p-toluenesulfonyloxy)-23,24-dinorcholane-8β-ol (3). A solution of diol 2 (1 g, 4.71 mmol) in anhydrous pyridine (12 mL) was cooled to −25° C. and a precooled solution of tosyl chloride (1.08 g, 5.66 mmol) in anhydrous pyridine (2 mL) was added dropwise. The reaction mixture was stirred at that temperature for 4 h and allowed to warm to 0° C. and stirred at that temperature for additional 20 h. The mixture was diluted with $CH_2Cl_2$ (50 mL) and washed with saturated $CuSO_4$ solution (30 mL), 1N HCl (30 mL), water (50 mL). The organic phase was dried ($NaSO_4$), filtered and concentrated. Purification by silica gel chromatography (25% ethyl acetate/hexane) yielded 1.7 g (4.64 mmol, 98%) of hydroxyl tosylate 3. $^1$H NMR (400 MHz, CDCl$_3$) δ: 7.78.(2H, d, J=8.2 Hz), 7.35 (2H, d, J=8.2 Hz), 4.06 (1H, m), 3.95 (1H, dd, J=9.2 and 3.0 Hz), 3.8 (1H, dd, J=9.2 and 6.2 Hz), 2.45 (3H, s), 0.96 (3H, d, J=6.6 Hz), 0.89 (3H, s); $^{13}$C NMR (100 MHz, CDCl$_3$) δ: 144.7, 133.0, 129.8, 127.9, 75.6, 69.0, 60.4, 52.2, 41.9, 40.1, 35.7, 33.5, 26.4, 22.4, 21.6, 17.3, 16.7, 13.41 MS m/z (relative integration): 366 (M+, 6), 194(14), 179(16), 125(30), 111(100).

Des-A,B-8β-(triethysilyloxy)-22-(p-toluenesulfonyloxy)-23,24-dinorcholane (4). To a −50° C. cooled solution of hydroxyl tosylate 3 (1.7 g, 4.64 mmol) in anhydrous $CH_2Cl_2$ (20 mL) was added 2,6-lutidine (0.64 mL, 5.57 mmol) followed by TESOTf (1.26 mL, 1.47 g, 5.57 mmol). The solution was stirred at 0° C. for 15 min and water (10 mL) was added. The mixture was extracted with $CH_2Cl_2$ (3×40 mL), and combined organic phases were washed with 1N aqueous solution of NaOH (40 mL) dried ($Na_2SO_4$), filtered and concentrated. The residue was purified by silica gel column chromatography (5% ethyl acetate/hexane) to give 1.87 g (3.89 mmol, 84%) of O-silylated tosylate 4. $^1$H NMR (400 MHz, CDCl$_3$) δ: 7.77 (2H, d, J=8.2 Hz), 7.33 (2H, d, J=8.2 Hz), 4.01(1H, m) 3.95(1H, dd, J=9.2 and 3.0 Hz), 3.78 (1H, dd, J=9.2 and 6.4 Hz), 2.43 (3H, s), 0.94 (3H, d, J=7.0 Hz), 0.93 (9H, t, J=7.9 Hz), 0.85 (3H, s), 0.53 (6H, q, J=7.9 Hz); $^{13}$C NMR (100 MHz, CDCl$_3$) δ: 144.5, 133.1, 129.7, 127.9, 75.7, 69.1, 52.7, 52.4, 42.1, 40.4, 35.7, 34.5, 26.5, 22.9, 21.6, 17.5, 16.7, 13.4, 6.9, 4.9; MS m/z (relative integration): 480 (M+, 30), 437 (50), 279 (49.), 257 (49), 257 (84), 177 (100); exact mass calculated for $C_{26}H_{44}SSi$ (M+) is 480.2730, found 480.2741.

Des-A,B-8β-(triethylsilyloxy)-23,24-dinorcholane-22-al (5). A solution of O-silylated tosylate 4 (1.8 g, 3.75 mmol) in DMSO (5 mL) was added to a suspension of $NaHCO_3$ (1.42 g, 16.8 mmol) in DMSO (20 mL) at rt. The mixture was heated to 150° C. under argon for 15 min and cooled to rt. Water (50 mL) followed by ethyl acetate (50 mL) were added and aqueous phase was extracted by ethyl acetate (3×30 mL). The combined organic phases were dried ($Na_2SO_4$), filtered and concentrated. The residue was purified by column chromatography (2% ethyl acetate/hexane) to afford 0.92 g (2.83 mmol, 76%) of O silylated aldehyde 5. $^1$H NMR (500 MHz, CDCl$_3$) δ: 9.58 (1H, d, J=3.2 Hz), 4.06 (1H, m), 2.35 (1H, m), 1.09 (3H, d, J=6.8 Hz), 0.96 (3H, s), 0.95 (9H, t, J=8.1 Hz), 0.55 (6H, q, J=8.1 Hz); $^{13}$C NMR (100 MHz, CDCl$_3$) δ: 205.5, 69.0, 52.3, 51.7, 49.2, 42.6, 40.5, 34.5, 26.2, 23.3, 17.6, 13.9, 13.3, 6.9, 4.9; MS m/z (relative integration): no M+, 295 (M+-C$_2$H$_5$, 41), 163 (100), 135 (35), 103 (72); exact mass calculated for $C_{17}H_{31}O_2Si$ ([M-C$_2$H$_5$]+) is 295.2093, found 295.2095.

Des-A,B-8β-(triethylsilyloxy)-pregnan-20-one (6). A flame dried flask was charged with KO-t-Bu (1.55 g, 13.9 mmol) and anhydrous t-BuOH (30 mL). $O_2$ was bubbled through the solution for 15 min. A solution of O-silylated aldehyde 5 (0.9 g, 2.78 mmol) in anhydrous t-BuOH (15 mL) was added to the reaction mixture and $O_2$ was bubbled through the solution for additional 10 min. The solution was quenched with water (15 ml) and extracted with ether (3×30 mL). The combined organic phases were dried ($Na_2SO_4$), filtered and concentrated. The residue was purified by column chromatography (3% ethyl acetate/hexane) to give 0.53 g (1.7 mmol, 62%) of the O-silylated 20-ketone 6. $^1$H NMR (500 MHz, CDCl$_3$) δ: 4.07 (1H, m), 2.46 (1H, t, J=9.0 Hz), 2.09 (3H, s), 0.94 (9H, t, J=8.0 Hz), 0.85 (3H, 3), 0.55 (6H, q, J=8.0 Hz); $^{13}$C NMR (100 MHz, CDCl$_3$) δ: 209.6, 68.9, 64.5, 53.2, 43.7, 39.9, 34.4, 31.5, 23.1, 21.8, 17.6, 15.3, 6.9, 4.9; MS m/z (relative intensity): 310 (M+, 12), 281 (100), 267 (59), 103 (98); exact mass calculated for $C_{18}H_{34}O_2Si$ (M+) is 310.2328, found 310.2325.

Des-A,B-20-methyl-8β-(triethylsilyloxy)-pregnan-20-ol (7). To a solution of Ketone 6 (0.5 g, 1.61 mmol) in dry THF (10 mL) was added 3M solution of methylmagnesiumbromide in diethyl ether (1.3 mL, 0.48 g, 4.03 mmol) at 0° C. under argon atmosphere. The reaction was allowed to come to room temperature and allowed to stir at that temperature for 2 h. Then it was quenched with saturated ammonium chloride solution. The mixture was extracted with ethyl acetate (3×20 mL). The combined organic extracts were washed with water (30 mL) and brine solution (30 mL). It was dried ($Na_2SO_4$), filtered and concentrated. The residue was purified by column chromatography (10% ethyl acetate/hexane) to give 0.42 g (1.29 mmol, 80%) of the tertiary alcohol 7. $^1$H NMR (400 MHz, CDCl$_3$) δ: 4.05 (1H, m), 2.05 (1H, m), 1.29 (3H, s), 1.17 (3H, s), 1.10 (3H, s), 0.95 (9H, t, J=7.9 Hz), 0.55 (6H, q, J=7.9 Hz); $^{13}$C NMR (100 MHz, CDCl$_3$) δ: 73.1, 69.0, 60.1, 52.6, 42.5, 40.7, 34.1, 30.5, 29.5, 22.3, 21.7, 17.2, 14.9, 6.5, 4.5; MS m/z (relative intensity): 326 (M+, 2), 311 (4), 297 (31), 279 (100); exact mass calculated for $C_{17}H_{33}O_2Si$ ([M-C$_2$H$_5$]+) is 297.2250, found 297.2246.

Des-A,B-20-methyl-pregnan-17(20)-ene-8β-ol (8). A mixture of compound 7 (0.150 g, 0.46 mmol), 2M hydrochloric acid (5 mL) and THF (5 mL) were refluxed at 70° C. for 1 h. THF was evaporated in vaccuo and the aqueous phase was basified using 2.5M NaOH solution. The aqueous phase was extracted with ethyl acetate (3×30 mL). The combined organic phases were washed with water (50 mL) and brine (30 mL). The organic phase was dried ($Na_2SO_4$), filtered and concentrated. The residue was purified by column chromatography (12% ethyl acetate/hexane) followed by HPLC (9.4 mm×25 cm zorbax-sil column, 4 ml/min) using hexane:IPA (95.5:0.5) solvent system. Pure alcohol 80.041 g (0.21 mmol, 46%) was eluted at $R_v$=56 mL. $^1$HNMR(500 MHz, CDCl$_3$) δ: 4.16 (1H, m), 2.28 (2H, m), 2.18 (1H, m), 1.70 (3H, s), 1.55 (3H, s), 1.10 (3H, s).

Des-A,B-20-methyl-pregnan-17(20)-ene-8-one (9). To a solution of alcohol 8 (0.020 g, 0.10 mmol) in anhydrous $CH_2Cl_2$ (5 mL) was added PDC (0.054 g, 0.14 mmol) at rt. After stirring the reaction for 3 h under argon atmosphere the solution was passed through a pad of celite with ethyl acetate. The filtrate was concentrated and applied on a Sep-Pak cartridge and eluted with ethyl acetate/hexane (6%) to give ketone as colourless oil. The ketone was purified on HPLC (6.2 mm×25 cm zorbax-sil column, 4 ml/min) using 4% ethyl acetate/hexane solvent system. Pure ketone 9 15.4 mg (0.08 mmol, 78%) was eluted at $R_v$=42 mL as colorless oil. $^1$H NMR (500 MHz, CDCl$_3$) δ: 2.57 (1H, m), 1.74 (3H, s), 1.59 (3H, m), 0.083 (3H, s), MS m/z (relative intensity): 192 (M+, 98), 177 (88), 159 (100), 149 (91), 107 (89); exact mass calculated for $C_{13}H_{20}O$ (M+) is 192.1514, found 192.1521.

1α-hydroxy-20-methyl-2-methylene-17(20)-ene-19-nor-pregnancalciferol (12). To a solution of phosphine oxide 10 (0.030 g, 0.05 mmol) in anhydrous THF (500 μL) at −25° C. was slowly added PhLi (34 μL, 5 mg, 0.061 mmol) under argon with stirring. The solution turned deep orange. The mixture was stirred at that temperature for 20 min and cooled to −78° C. A precooled (−78° C.) solution of ketone 9 (0.004 g, 0.02 mmol) in anhydrous THF (100 μL) was added slowly. The mixture was stirred under argon atmosphere at −78° C. for 3 h and at 0° C. for 18 h. Ethyl acetate was added and organic phase was washed with brine, dried ($Na_2SO_4$) and evaporated. The residue was applied on a Sep-Pak cartridge, and eluted with 1% ethyl acetate/hexane to give the 19-nor protected vitamin derivative (1 mg of unreacted ketone was recovered). The vitamin was further purified by HPLC (6.2 mm×25 cm zorbax-sil column, 4 ml/min) using hexane/ethyl acetate (99.05:0.05) solvent system. Pure compound 11, 3.6 mg (0.0067 mmol, 41%) was eluted at $R_v$=28 mL as colourless oil. UV (in hexane): $\lambda$max 244, 252, 262 nm; $^1$H NMR (500 MHz, $CDCl_3$) δ: 6.21 and 5.87 (1H and 1H, each d, J=11.4 Hz), 4.97 and 4.92 (2H, each s), 4.43 (2H, m), 2.80 (1H, m), 2.53 (1H, dd, J=13.8 and 5.6 Hz), 2.452 (1H, dd, J=8.2 and 5.6 Hz), 1.71 (3H, s), 1.58 (3H, s), 0.9, 0.84 (9H and 9H, each s), 0.74 (3H, s), 0.027, 0.050, 0.068, 0.081 (Each 3H, each s).

The protected vitamin 11 (0.0036 g, 0.0067 mmol) was dissolved in anhydrous THF (500 μL) and treated with TBAF (66 μL, 18 mg, 0.067 mmol) and stirred at rt in dark for overnight. The solvent was removed in vaccuo and residue was applied on Sep-Pak cartridge, and eluted with 30% ethyl acetate/hexane to get the deprotected vitamin. The vitamin was further purified by HPLC (6.2 mm×25 cm zorbax-sil column, 4 ml/min) using hexane/IPA (90/10) as solvent system. Pure vitamin 12, 1.3 mg (0.0036 mmol, 61%) was eluted at $R_v$=26 mL. UV (in ethanol): $\lambda_{max}$, 243, 251, 261 nm; $^1$H NMR (500 MHz, $CDCl_3$) δ: 6.35 and 5.92 (1H and 1H, each d, J=11.3 Hz), 5.10 and 5.13 (1H and 1H, each s), 4.48 (2H, m), 2.88 (1H, dd, J=13.3 and 4.5Hz), 2.78 (1H, dd, J=12.6 and 3.6 Hz), 2.58 (1H, dd, J=12.7 and 3.6 Hz), 2.13 (1H, m), 1.71 (3H, s), 1.61 (3H, s), 0.739 (3H, s); MS m/z (relative intensity): 328 ($M^+$, 100), 313 (23), 310 (15), 295 (11), 277 (8), 243 (35), 229 (41), 149 (83); exact mass calculated for $C_{22}H_3O_2Na$ ($[MNa]^+$) is 351.2300, found 351.2304.

BIOLOGICAL ACTIVITY OF 2-METHYLENE-19-NOR-1α-HYDROXY-17-ENE-HOMOPREGNACALCIFEROL

The introduction of a methylene group to the 2-position, the introduction of a double bond between the 17 and 20 positions, and the elimination of carbons 23, 24, 25, 26 and 27 in the side chain of 1α-hydroxy-19-nor-vitamin $D_3$ had little or no effect on binding to the full length recombinant rat vitamin D receptor, as compared to 1α,25-dihydroxyvitamin $D_3$. The compound VIT-I bound equally well to the receptor as compared to the standard 1,25-$(OH)_2D_3$ (FIG. 1). It might be expected from these results that compound VIT-I would have equivalent biological activity. Surprisingly, however, compound VIT-I is a highly selective analog with unique biological activity.

Figure 6:
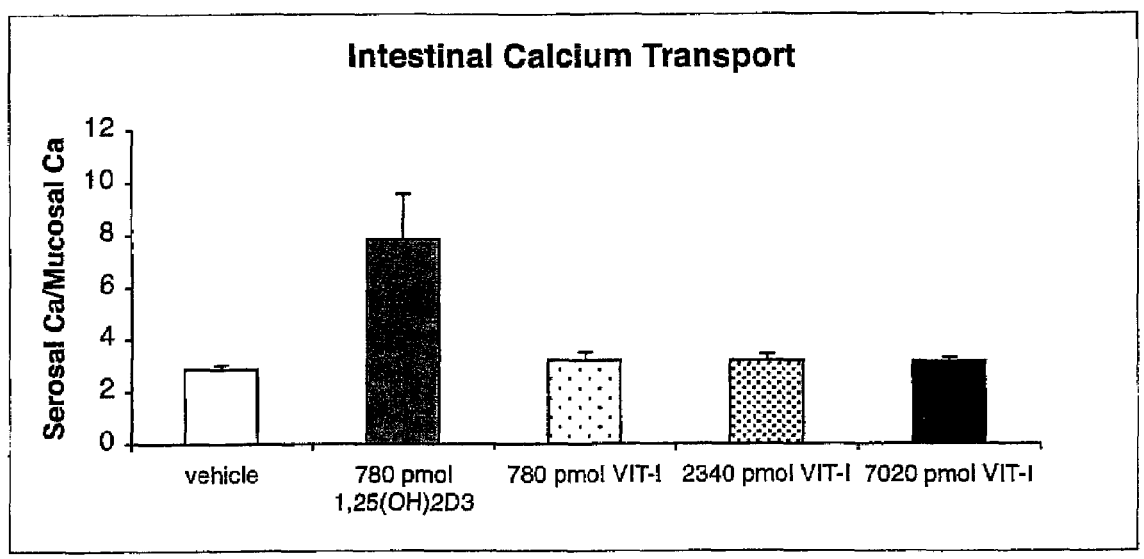

FIG. 6 shows that VIT-I has very little activity as compared to that of 1,25-dihydroxyvitamin $D_3$ (1,25$(OH)_2D_3$), the natural hormone, in stimulating intestinal calcium transport.

Figure 4:
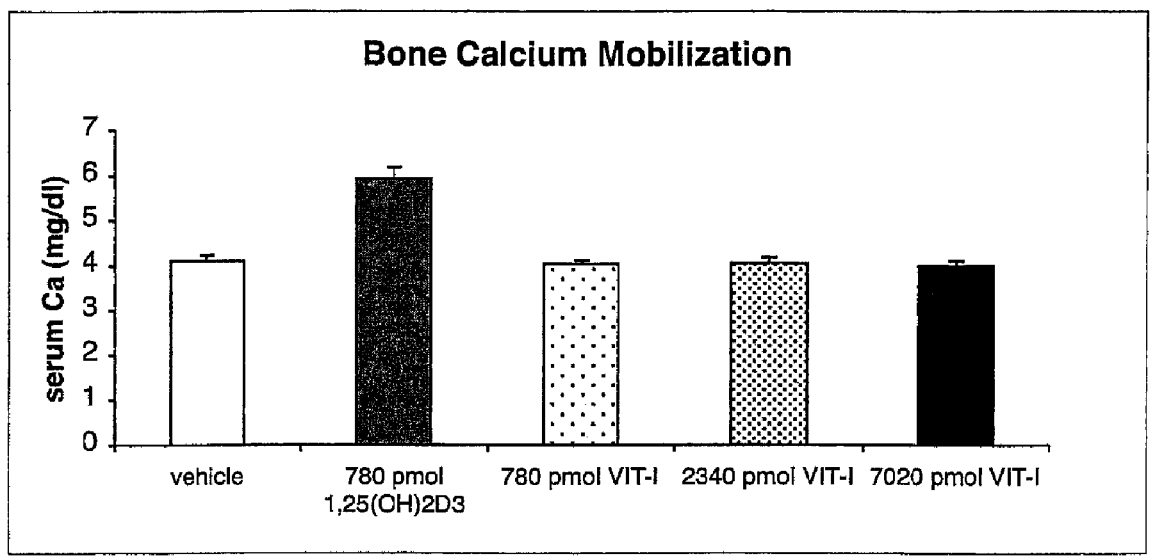
Figure 5:
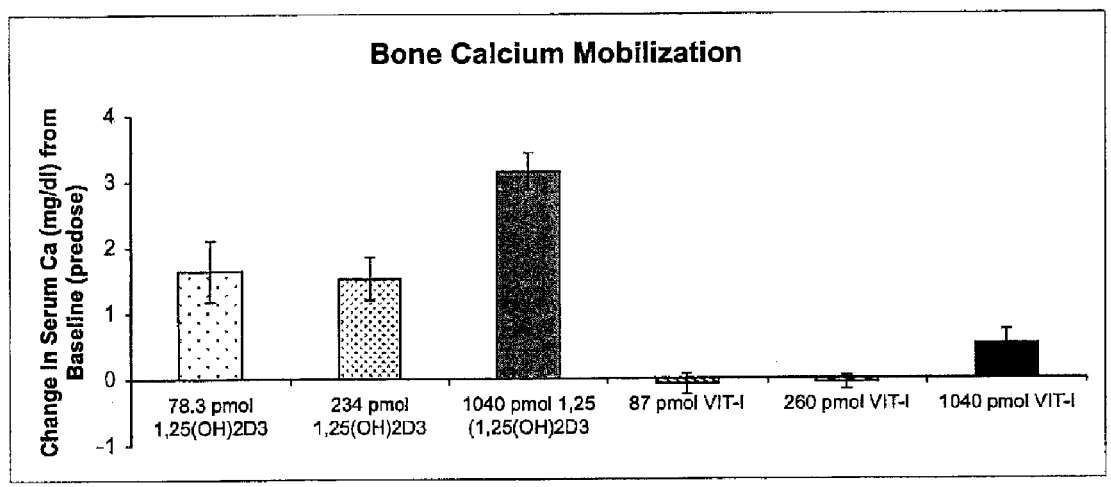

FIGS. 4 and 5 demonstrate that VIT-I has very little bone calcium mobilization activity, as compared to 1,25$(OH)_2D_3$.

FIGS. 4-6 thus illustrate that VIT-I may be characterized as having little, if any, calcemic activity.

Figure 2:
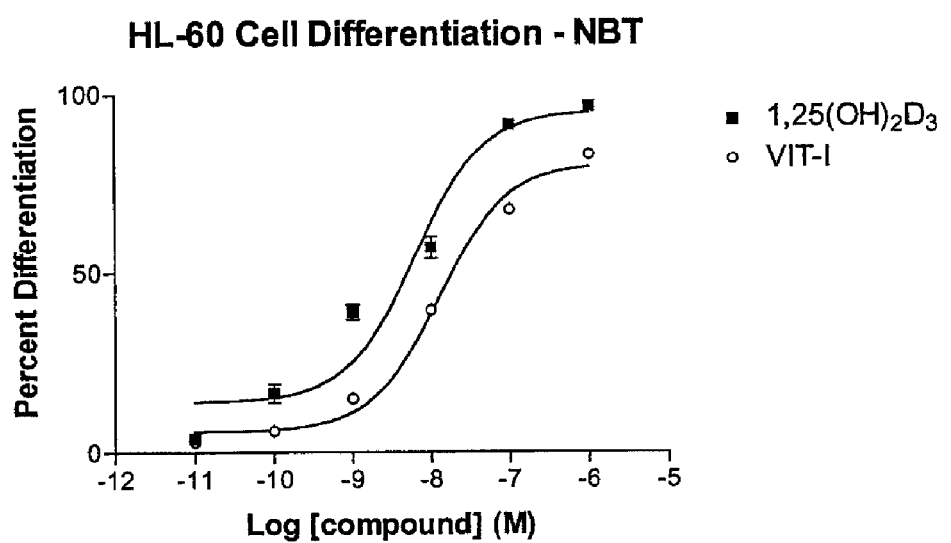

FIG. 2 illustrates that VIT-I is almost as potent as 1,25(OH)$_2D_3$ on HL-60 cell differentiation, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
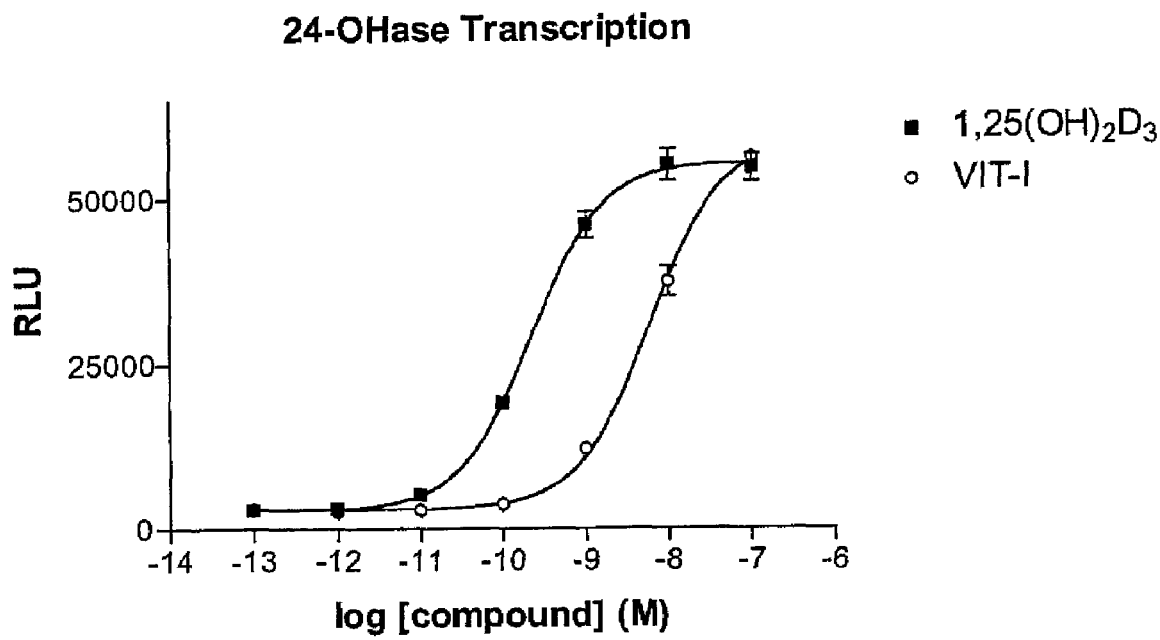

FIG. 3 illustrates that the compound VIT-I has transcriptional activity in bone cells, albeit lower than 1α,25-dihydroxyvitamin $D_3$. This result, together with the cell differentiation activity of FIG. 2, suggests that VIT-I will be very effective in psoriasis because it has direct cellular activity in causing cell differentiation and in suppressing cell growth. These data also indicate that VIT-I may have significant activity as an anti-cancer agent, especially against leukemia, colon cancer, breast cancer, skin cancer and prostate cancer.

The strong activity of VIT-I on HL-60 differentiation and in vitro transcription suggests it will be active in suppressing growth of parathyroid glands and in the suppression of the preproparathyroid gene.

Experimental Methods

Vitamin D Receptor Binding

Test Material

Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol ($\leq 0.2\%$) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca)+AEK for one week followed by Diet 11 (0.02% Ca)+AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR binding, HL60 cell differentiation, and transcription activity. VIT-I ($K_i=1.9\times10^{-10}$M) is nearly equivalent to the natural hormone 1α,25-dihydroxyvitamin $D_3$ ($K_i=7.8\times10^{-11}$M) in its ability to compete with [$^3$H]-1,25(OH)$_2$D$_3$ for binding to the full-length recombinant rat vitamin D receptor (FIG. 1). There is also little difference between VIT-I ($EC_{50}=1.3\times10^{-8}$M) in its ability (efficacy or potency) to promote HL60 differentiation as compared to 1α,25-dihydroxyvitamin $D_3$ ($EC_{50}=6.2\times10^{-9}$M) (See FIG. 2). Compound VIT-I ($EC_{50}=6.0\times10^{-9}$M) has transcriptional activity in bone cells but noticeably lower than 1α,25-dihydroxyvitamin $D_3$ ($EC_{50}=2.2\times10^{-10}$M) (See FIG. 3). These results suggest that VIT-I will be very effective in psoriasis because it has direct cellular activity in causing cell differentiation and in suppressing cell growth. These data also indicate that VIT-I will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of VIT-I and 1,25(OH)$_2$D$_3$ in intestine and bone were tested. As expected, the native hormone (1,25(OH)$_2$D$_3$) increased serum calcium levels at all dosages (FIG. 4). FIG. 4 and FIG. 5 show that VIT-I has little, if any, activity in mobilizing calcium from bone. Administration of VIT-I at 780 pmol/day for 4 consecutive days did not result in mobilization of bone calcium, and increasing the amount of VIT-I to 2340 pmol/day and then to 7020 pmol/day was also without any substantial effect.

Intestinal calcium transport was evaluated in the same groups of animals using the everted gut sac method (FIG. 6). These results show that the compound VIT-1 does not promote intestinal calcium transport when administered at 780 pmol/day, 2340 pmol/day or 7020 pmol/day, whereas 1,25(OH)$_2$D$_3$ promotes a significant increase at the 780 pmol/day dose. Thus, it may be concluded that VIT-I is essentially devoid of intestinal calcium transport activity at the tested doses.

These results illustrate that VIT-I is an excellent candidate for numerous human therapies as described herein, and that it may be particularly useful in a number of circumstances such as suppression of secondary hyperparathyroidism of renal osteodystrophy, autoimmune diseases, cancer, and psoriasis. VIT-I is an excellent candidate for treating psoriasis because: (1) it has significant VDR binding, transcription activity and cellular differentiation activity; (2) it is devoid of hypercalcemic liability unlike 1,25(OH)$_2$D$_3$; and (3) it is easily synthesized. Since VIT-I has significant binding activity to the vitamin D receptor, cell differentiation activity, and gene transcription activity but has little ability to raise blood serum calcium, it may also be particularly useful for the treatment of secondary hyperparathyroidism of renal osteodystrophy.

These data also indicate that the compound VIT-I of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound VIT-I of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly VIT-I, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly VIT-I, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly VIT-I, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually or parenterally in dosages of from about 0.01 µg/day to about 1000 µg/day, and preferably from about 0.1 µg/day to about 500 µg/day.

The compounds I, particularly VIT-I, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly VIT-1, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating obesity of an animal, inhibiting adipocyte differentiation, inhibiting SCD-1 gene transcription, and/or reducing body fat in an animal comprising administering to an animal in need thereof an effective amount of a compound having the formula

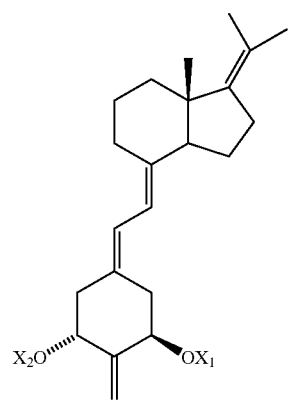

where $X_1$ and $X_2$, which may be the same or different, are each selected from hydrogen or a hydroxy-protecting group.

2. The method of claim 1 wherein the compound is administered orally.

3. The method of claim 1 wherein the compound is administered parenterally.

4. The method of claim 1 wherein the compound is administered transdermally.

5. The method of claim 1 wherein the compound is administered rectally.

6. The method of claim 1 wherein the compound is administered nasally.

7. The method of claim 1 wherein the compound is administered sublingually.

8. The method of claim 1 wherein the compound is administered in a dosage of from about 0.01 μg/day to about 1000 μg/day.

9. The method of claim 1 wherein the compound is 2-methylene-19-nor-1α-hydroxy-17-ene-homopregnacalciferol having the formula 10. The method of claim 1 wherein the animal is a human.

11. The method of claim 1 wherein the animal is a domestic animal.

12. The method of claim 1 wherein the animal is an agricultural animal.

13. A method of treating acne in an animal, the method comprising administering to an animal in need thereof an effective amount of a compound having the formula where $X_1$ and $X_2$, which may be the same or different, are each selected from hydrogen or a hydroxy-protecting group.

14. The method of claim 13 wherein the compound is administered orally.

15. The method of claim 13 wherein the compound is administered parenterally.

16. The method of claim 13 wherein the compound is administered transdermally.

17. The method of claim 13 wherein the compound is administered rectally.

18. The method of claim 13 wherein the compound is administered nasally.

19. The method of claim 13 wherein the compound is administered sublingually.

20. The method of claim 13 wherein the compound is administered in a dosage of from about 0.01 μg/day to about 1000 μg/day.

21. The method of claim 13 wherein the compound is 2-methylene-19-nor-1α-hydroxy-17-ene-homopregnacalciferol having the formula:

22. A method of treating hypertension in an animal, the method comprising administering to an animal in need thereof an effective amount of a compound having the formula where $X_1$ and $X_2$, which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 µg/day to about 1000 µg/day.

30. The method of claim 22 wherein the compound is 2-methylene-19-nor-1α-hydroxy-17-ene-homopregnacalciferol having the formula:

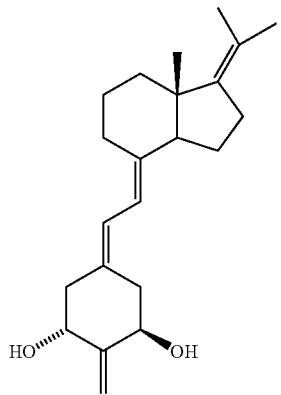

* * * * *